US009811897B2

(12) United States Patent
Harada et al.

(10) Patent No.: US 9,811,897 B2
(45) Date of Patent: Nov. 7, 2017

(54) DEFECT OBSERVATION METHOD AND DEFECT OBSERVATION DEVICE

(71) Applicant: HITACHI HIGH-TECHNOLOGIES CORPORATION, Minato-ku, Tokyo (JP)

(72) Inventors: Minoru Harada, Tokyo (JP); Yuji Takagi, Tokyo (JP); Ryo Nakagaki, Tokyo (JP); Takehiro Hirai, Tokyo (JP); Hirohiko Kitsuki, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 14/652,198

(22) PCT Filed: Dec. 6, 2013

(86) PCT No.: PCT/JP2013/082753
§ 371 (c)(1),
(2) Date: Jun. 15, 2015

(87) PCT Pub. No.: WO2014/119124
PCT Pub. Date: Aug. 7, 2014

(65) Prior Publication Data
US 2015/0332445 A1 Nov. 19, 2015

(30) Foreign Application Priority Data

Jan. 30, 2013 (JP) ................................. 2013-014990

(51) Int. Cl.
*G06T 7/00* (2017.01)
*G01N 21/95* (2006.01)
(52) U.S. Cl.
CPC ......... *G06T 7/001* (2013.01); *G01N 21/9501* (2013.01); *G06T 2207/10004* (2013.01);
(Continued)

(58) Field of Classification Search
CPC ........... G06T 2207/30148; G06T 7/001; G06T 2207/10061; G06T 7/0004;
(Continued)

(56) References Cited

U.S. PATENT DOCUMENTS

2002/0051565 A1\* 5/2002 Hiroi ................ G01N 21/95607
382/149
2003/0021462 A1 1/2003 Sakai et al.
(Continued)

FOREIGN PATENT DOCUMENTS

JP 8-21803 A 1/1996
JP 2000-105203 A 4/2000
(Continued)

OTHER PUBLICATIONS

International Search Report from International Patent Application No. PCT/JP2013/082753, Mar. 11, 2014.

*Primary Examiner* — Kim Vu
*Assistant Examiner* — Michael Vanchy, Jr.
(74) *Attorney, Agent, or Firm* — Miles & Stockbridge P.C.

(57) ABSTRACT

The purpose of the present invention is to easily extract, from samples to be observed, defect candidates that can be labeled as a defect or "nuisance" (a part for which a manufacturing tolerance or the like is erroneously detected) and to allow parameters pertaining to observation processing to be easily adjusted. This defect observation method comprises: an imaging step to image, on the basis of defect information from an inspection device, an object to be inspected and obtain a defect image and a reference image corresponding to the defect image; a parameter determining step to determine a first parameter to be used in the defect extraction by using a first feature set distribution acquired from the reference image and the defect image captured in the imaging step and a second feature net distribution (Continued)

acquired from the reference image; and an observing step to observe using the first parameter determined in the parameter determining step. The present invention can be applied to a method of observing defects generated during the manufacturing of semiconductor wafers.

12 Claims, 14 Drawing Sheets

(52) U.S. Cl.
CPC .............. *G06T 2207/10061* (2013.01); *G06T 2207/30148* (2013.01)

(58) Field of Classification Search
CPC ........ G06T 2207/20021; G06T 7/0002; G01N 21/9501; G01N 2021/8887; G01N 21/95607; G01N 21/8851; G01N 21/956; G01N 2223/611; G01N 23/225; G01R 31/2894; H01J 2237/2817; H01J 37/28; H01J 37/244; G06K 9/6857

See application file for complete search history.

(56) References Cited

U.S. PATENT DOCUMENTS

| | | | |
|---|---|---|---|
| 2007/0121106 A1* | 5/2007 | Shibata | G01N 21/8806 356/237.2 |
| 2011/0163230 A1* | 7/2011 | Hiroi | H01J 37/20 250/310 |
| 2012/0027285 A1* | 2/2012 | Shlain | G06K 9/6256 382/149 |

FOREIGN PATENT DOCUMENTS

| | | |
|---|---|---|
| JP | 2001-189358 A | 7/2001 |
| JP | 2007-040910 A | 2/2007 |
| JP | 2007-225531 A | 9/2007 |

* cited by examiner

FIG. 14
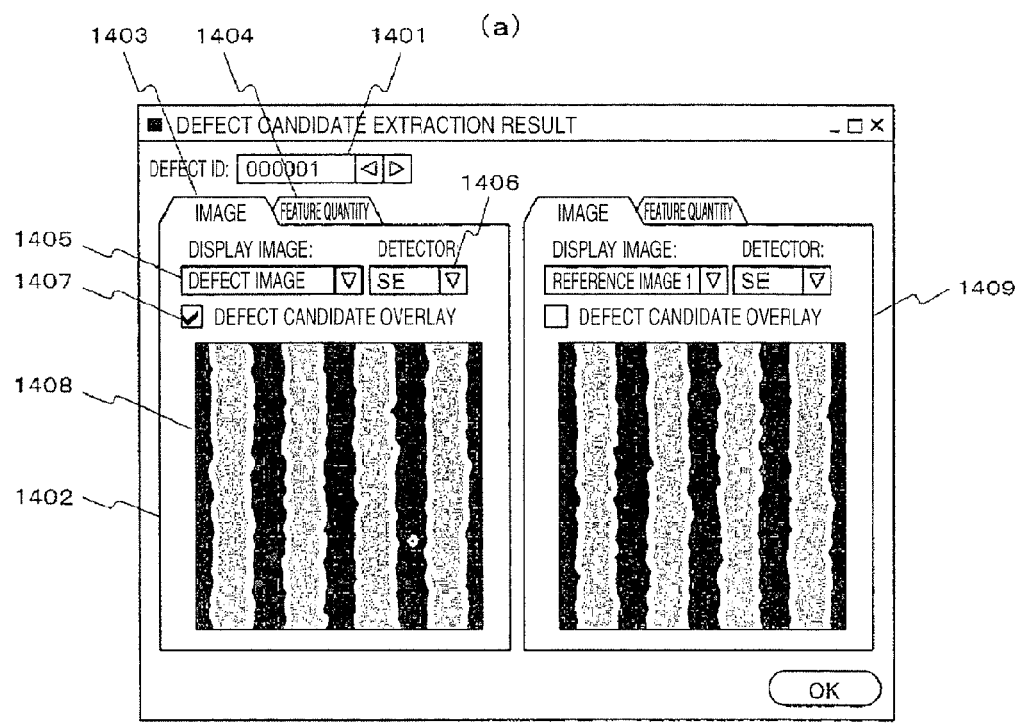
(a)
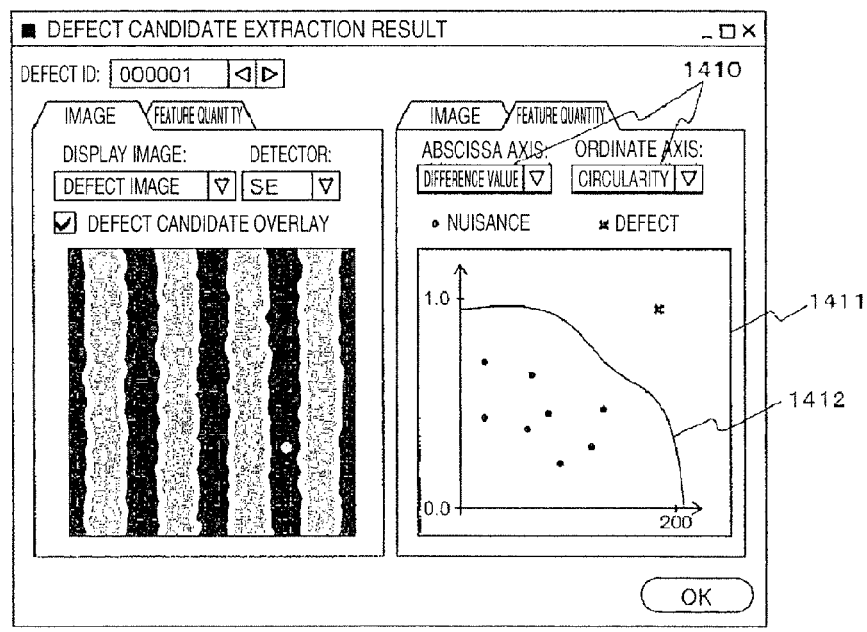
(b)

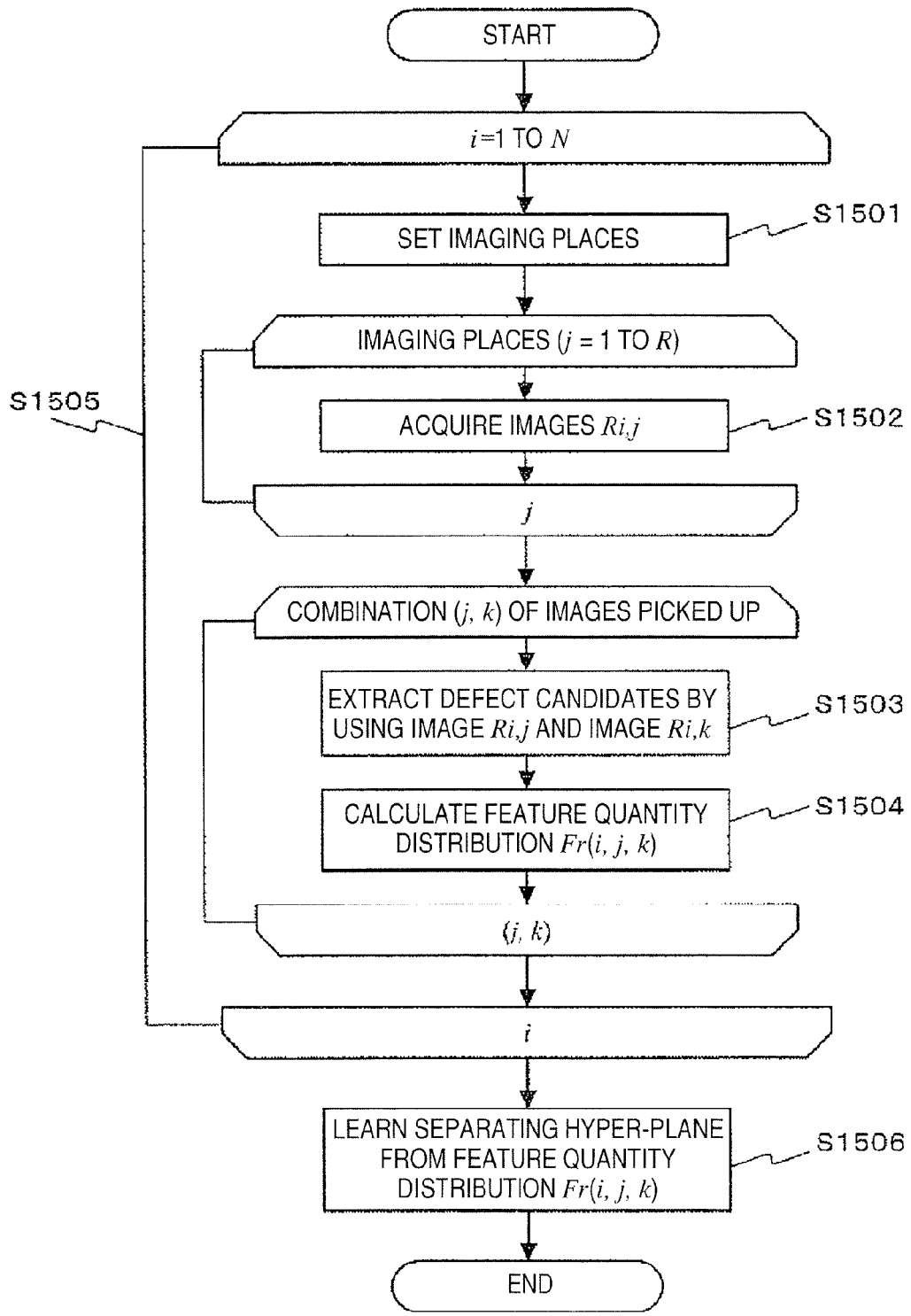

DEFECT OBSERVATION METHOD AND DEFECT OBSERVATION DEVICE

TECHNICAL FIELD

The present invention relates to a method and device for observing defects caused in manufacture of a semiconductor wafer.

BACKGROUND ART

In manufacture of a semiconductor wafer, it is important for securing a profit to start a manufacture process rapidly and make a shift to mass production system of high yield early.

In order to achieve this object, various inspection/measurement devices are introduced into manufacture lines. In the process start stage, it is conducted to, for example, change process conditions intentionally, making a plurality of wafers or chips, inspecting the wafers or chips, and determining process conditions on the basis of a result of the inspection, with the object of determining process conditions capable of forming a desired circuit pattern early.

On the other hand, wafer inspection in a mass production stage is conducted for monitoring. In other words, in an intermediate stage of wafer manufacture, a wafer is sampled and inspected, and it is checked whether a defect occurs on a surface of the wafer or whether there is an abnormality in a circuit pattern formed on the wafer surface. In a case where a defect or an abnormality in the circuit pattern is detected because of inspection, a cause thereof is investigated and a necessary countermeasure is taken.

As a representative inspection device used in such a process start stage or a mass production stage, there is an optical wafer inspection device. For example, JR-A-2000-105203 (Patent Literature 1) discloses a technique of picking up an optical image of a wafer surface by means of bright visual field illumination and inspecting a defect by comparing the optical image of the wafer surface with an image of a good article region (for example, an image of an adjacent chip). However, such an optical inspection device undergoes influence of an illumination wavelength thereof, and a resolution limit of an acquired image becomes approximately several hundred nanometers. As regards a defect of several ten nanometers order on the wafer, therefore, the optical inspection device can detect only whether there is a defect. When conducting a detailed defect analysis, a different defect observation device having a higher imaging resolution is needed.

The defect observation device is a device that picks up an image in a defect position on a wafer by using an output of the inspection device and outputs the image. In the semiconductor manufacture process, size shrinking is promoted. As a result, a defect size reaches an order of several nm. In order to observe a defect in detail, therefore, a resolution of several nm order is needed. Accordingly, an observation device (hereafter referred to as review SEM) using a scanning electron microscope (SEM) has been widely used in recent years. In a mass production line of semiconductor, automation of the observation work is desired. The review SEM mounts a function of ADR (Automatic Defect Review) for automatically collecting images in defect positions in a sample and ADC (Automatic Defect Classification) for automatically classifying approximately several hundred defect images acquired by the ADR according to occurrence causes or features of exterior view. By the way, a defect position coordinate (coordinate information indicating a position of a defect on the sample) output by the inspection device includes an error. Therefore, the ADR has a function of re-detecting a defect from an SEM image picked up with a wide visual field around a defect position coordinate output by the inspection device and picking up an image in the re-detected defect position with high magnification. As a method for detecting defects from the SEM image, JP-A-2001-189358 (Patent Literature 2) states a method of using an image obtained by picking up an image of an area where the same circuit pattern as that of a defect region is formed, as a reference image and detecting a defect by comparing an image obtained by picking up an image of defect region with the reference image. Furthermore, JP-A-2007-40910 (Patent Literature 3) states a method of detecting a defect from one image obtained by picking up an image of a defect region. As one method of automatic classification, JP-A-21803 (Patent Literature 4) states a method of quantizing an exterior view feature quantity of a defect region by conducting image processing and classifying defects by using a neural network. Furthermore, as a method capable of easily coping with even in a case where the number of kinds of defects to be classified is many, JP-A 2007-225531 (Patent Literature 5) states a method of classifying defects by combining a rule base classification method with a teaching classification method.

CITATION LIST

Patent Literature

PATENT LITERATURE 1: JP-A-2000-105203
PATENT LITERATURE 2: JP-A-2001-189358
PATENT LITERATURE 3: JP-A-2007-40910
PATENT LITERATURE 4: JP-A-8-21803
PATENT LITERATURE 5: JP-A-2007-225531

SUMMARY OF INVENTION

Technical Problem

As described above, the defect position coordinate output by the inspection device includes an error. In the defect observation device as well, therefore, it is necessary to re-detect the defect position from a picked up image. Patent Literature 1 states a method of calculating a variation of image signals as to corresponding pixels of structures having the same shape or neighboring pixels on the basis of detected image signals, setting a determination criterion (threshold) of a pixel signal level for determining whether there is a defect such as a foreign matter in accordance with the calculated variation, and determining whether there is a defect as to the image signal on the basis of the determination criterion.

With size shrinking and increased complexity in the semiconductor manufacture process, however, lowering of the defect detection rate poses a problem. For example, with the size shrinking, a size of a fatal defect also becomes minute. Therefore, it becomes difficult to distinguish a defect from a manufacture tolerance (such as, for example, line edge roughness) of a circuit pattern. Furthermore, if a device has a three-dimensional structure, a signal quantity from a lower layer becomes small, and consequently it becomes difficult to distinguish noise from a defect signal.

For conducting the distinguishing with high precision, analysis using a feature quantity is effective. Specifically, first, an area having a large light and shade difference between a defect image and a reference image (good article image) is extracted as a defect candidate by conducting light and shade comparison (as this method, a method stated in Patent Literature 1, Patent Literature 2, or Patent Literature 3 may be used). Defect candidates include regions where a manufacture tolerance or the like is detected falsely (hereafter referred to as nuisance) besides true defect regions. As regards each of extracted defect candidates, therefore, a feature (such as, for example, a light and shade value, an area, or a circularity) obtained from an image is quantified, and a defect and a nuisance are discriminated by using a discriminator. By the way, the discriminator may be configured by machine learning using a technique of pattern recognition. As the pattern recognition technique, for example, a neural network, an SVM (Support Vector Machine) or the like may be used. Or a discrimination rule may be generated automatically.

In general, for configuring a high precision discriminator by machine learning, it is necessary to indicate a large number of defect candidates labeled with "defect" and "nuisance." For a user to provide defect candidates detected by the light and shade comparison inspection with labels of "defect" and "nuisance," much labor is needed and it is not realistic. Therefore, it is an object of the present invention to provide a method and device for easily extracting defect candidates that can be labeled with "defect" and "nuisance" from samples of observation object and making parameters concerning observation processing adjustable simply.

Solution to Problem

In order to solve the above-described problem, for example, a configuration stated in claims is adopted.

The present application includes a plurality of means that solve the above-described problem. For example, a defect observation method includes an imaging process for imaging an inspection object on the basis of defect information from an inspection device and obtaining a defect image and a reference image corresponding to the defect image, a parameter determination process for determining a first parameter to be used in defect extraction by using first feature quantity distribution obtained from the defect image picked up in the imaging process and the reference image and second feature quantity distribution obtained from the reference image, and an observation process for conducting observation by using the first parameter determined in the parameter determination process.

Advantageous Effects of Invention

According to the present invention, it becomes possible to extract easily defect candidates that can be labeled with defect and nuisance from samples of the observation object.

Problems, configurations, and effects other than those described above will be clarified by ensuing description of embodiments.

BRIEF DESCRIPTION OF DRAWINGS

FIG. 14 is a GUI for confirming a result of defect detection; and

FIG. 15 is a processing flow for adjusting parameters.

DESCRIPTION OF EMBODIMENTS

Embodiment 1

Hereafter, defect observation processing concerning the present invention will be described. In the present embodiment, a method for acquiring an observation image of a defect with an imaging device having a scanning electron microscope (SEM) will be described. However, the imaging device concerning the present invention may be other than the SEM, and may be an imaging device using a charged particle beam such as ions.

Figure 1:
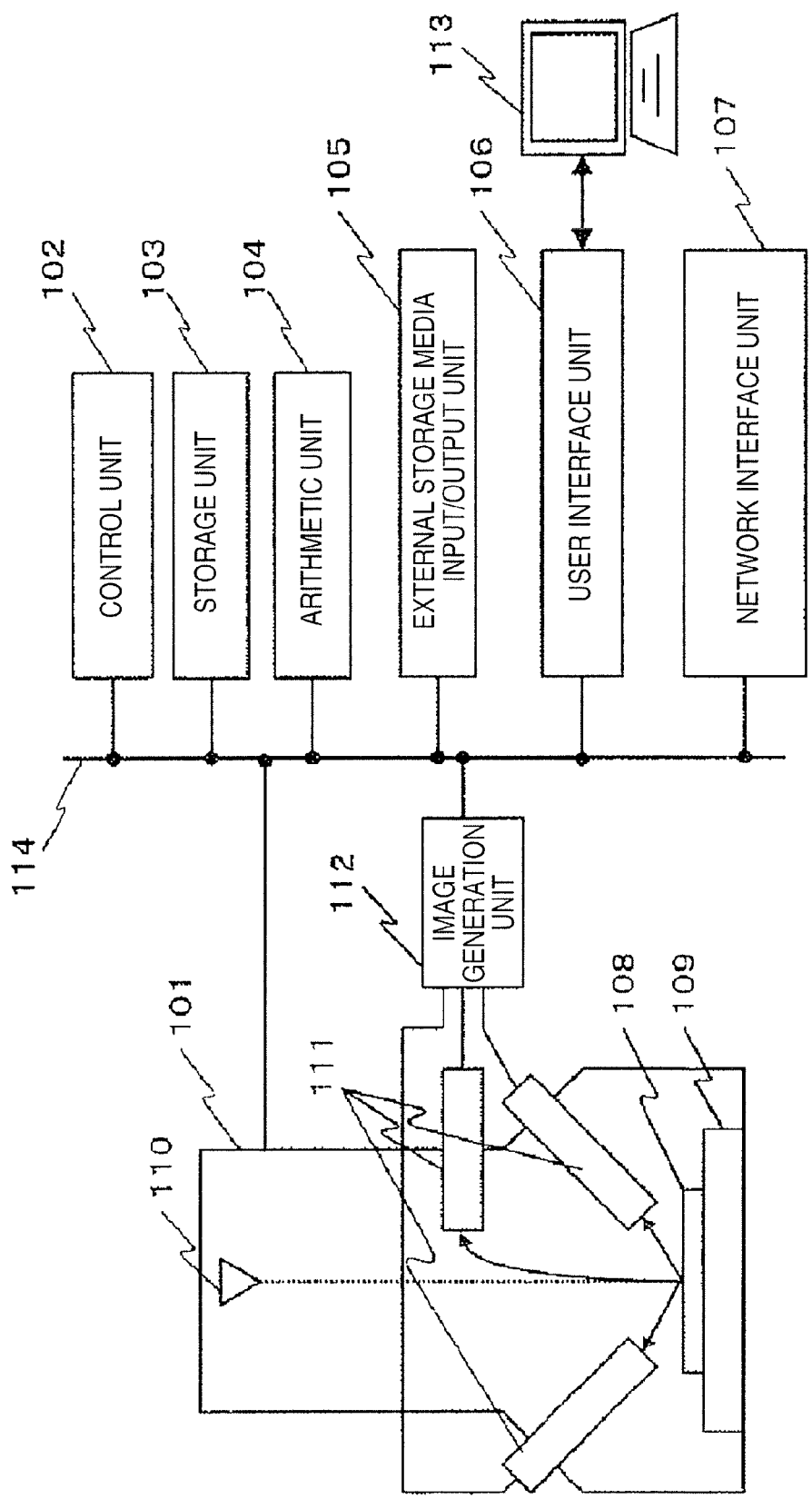
FIG. 1 is a configuration diagram of a defect observation device.

FIG. 1 represents a configuration diagram of a device according to the present invention. The device includes an SEM 101 to conduct picking up an image, a control unit 102 to exercise general control, a storage unit 103 to store information into a magnetic disk, a semiconductor memory or the like, an arithmetic unit 104 to conduct arithmetic operations in accordance with a program, an external storage media input/output unit 105 to conduct inputting/outputting of information to/from external storage media connected to the device, a user interface unit 106 to control inputting/outputting of information to/from a user, and a network interface unit 107 to conduct communication with another device or the like via a network. Furthermore, an input/output terminal 113 configured to have a keyboard, a mouse, a display, and so forth is connected to the user interface unit 106. The SEM 101 includes a movable stage 109 to mount a sample wafer 108, an electron source 110 to irradiate the sample wafer 108 with an electron beam, detectors 111 to detect secondary electrons, reflected electrons, and so forth generated from the sample wafer, an electron lens (not illustrated) to focus the electron beam onto the sample, a deflector (not illustrated) to scan the top of the sample wafer with the electron beam, and an image generation unit 112 to conduct digital conversion on a signal from the detector 111 and generate a digital image. By the way, these components are connected via a bus 114, and these components can conduct information giving/receiving with each other.

Figure 2:
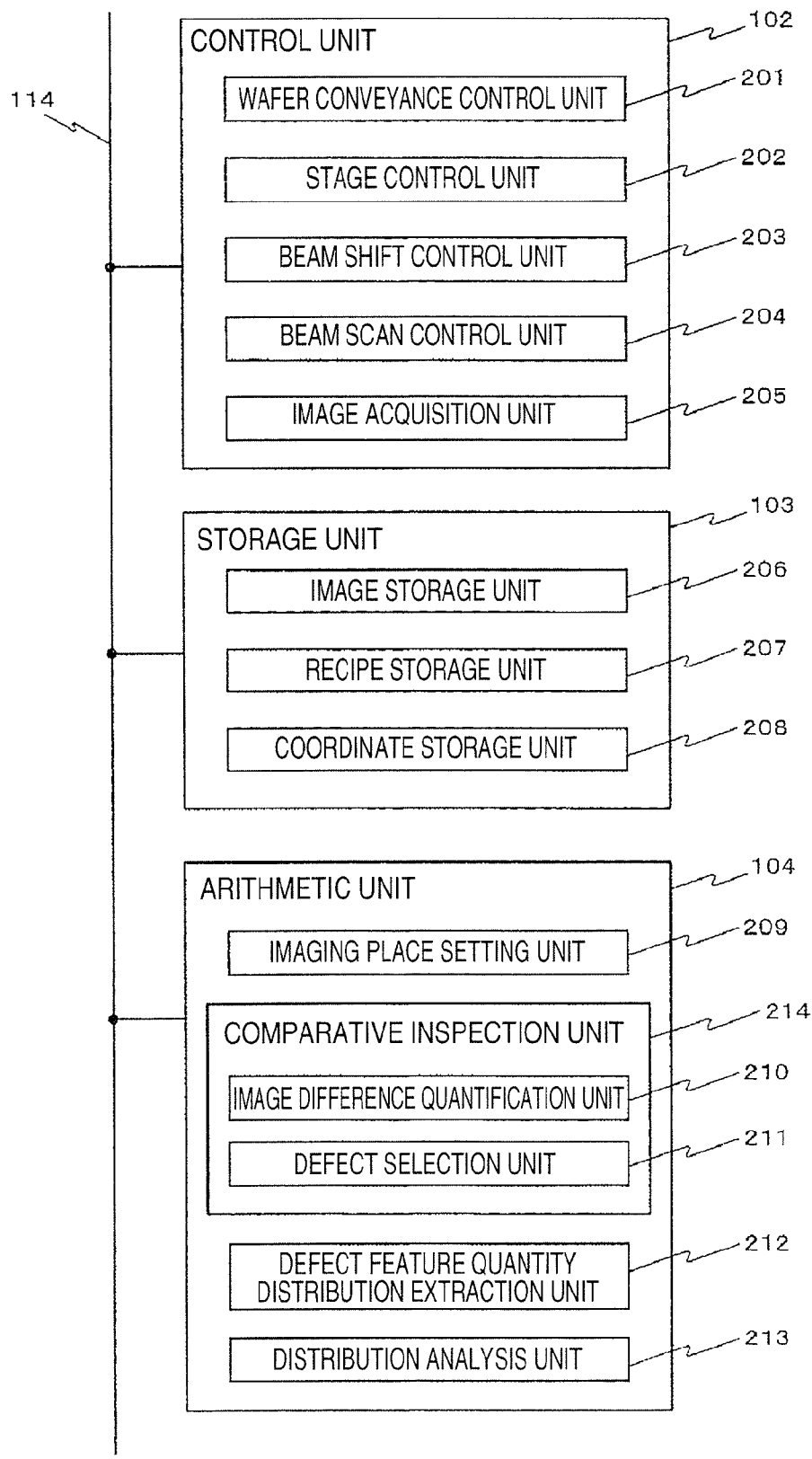
FIG. 2 is a configuration diagram of a control unit, a storage unit, and an arithmetic unit in the defect observation device.

FIG. 2 shows a configuration of the control unit 102, the storage unit 103, and the arithmetic unit 104. The control unit includes a wafer conveyance control unit 201 to control conveyance of a wafer, a stage control unit 202 to control a stage, a beam shift control unit 203 to control a position of irradiation with an electron beam, a beam scan control unit 204 to control scanning with the electron beam, and an image acquisition unit 205. The storage unit 103 includes an image storage unit 206 to store acquired image data, a recipe storage unit 207 to store imaging conditions (such as, for example, an acceleration voltage, a probe current, the number of added frames, and imaging visual field size), processing parameters, and so forth, and a measurement coordinate storage unit 208 to store a coordinate of an observed place. The arithmetic unit 104 includes an imaging place setting unit 209 to set a coordinate of a place to be imaged, a comparative inspection unit 214 to conduct comparative inspection on an image, a defect feature quantity distribution extraction unit 212 to extract feature quantity distribution in a defect region, and a distribution analysis unit 213 to analyze feature quantity distribution. Furthermore, the comparative inspection unit 214 includes an image difference quantification unit 210 to quantify a difference between images, and a defect region selection unit 211 to select a defect region from an image. By the way, the units 209 to 213 may be configured as hardware designed to conduct respective arithmetic operations. Or the units 209 to 213 may be configured to be mounted as software and executed by using a general-purpose arithmetic device (such as, for example, a CPU or a GPU).

A method for acquiring an image of a specified coordinate by using the image acquisition unit 205 will now be described. First, a robot arm places the wafer 108 that becomes a measurement object on the stage 109 under control of the wafer conveyance control unit 201. Subsequently, the stage control unit 202 moves the stage 109 to cause a beam irradiation range to include an imaging visual field. At this time, the stage position is measured to absorb a movement error of the stage. The beam control unit 203 adjusts the beam irradiation position to cancel the movement error. The electron beam is emitted from the electron source 110. The beam scan control unit 204 scans in the imaging visual field with the electron beam. Secondary electrons and reflected electrons generated from the wafer by irradiation with the beam are detected by the detector 111, and converted to a digital image by the image generation unit 112. The image storage unit 206 stores the picked up image together with incidental information such as the imaging condition and imaging date and hour.

Figure 3:
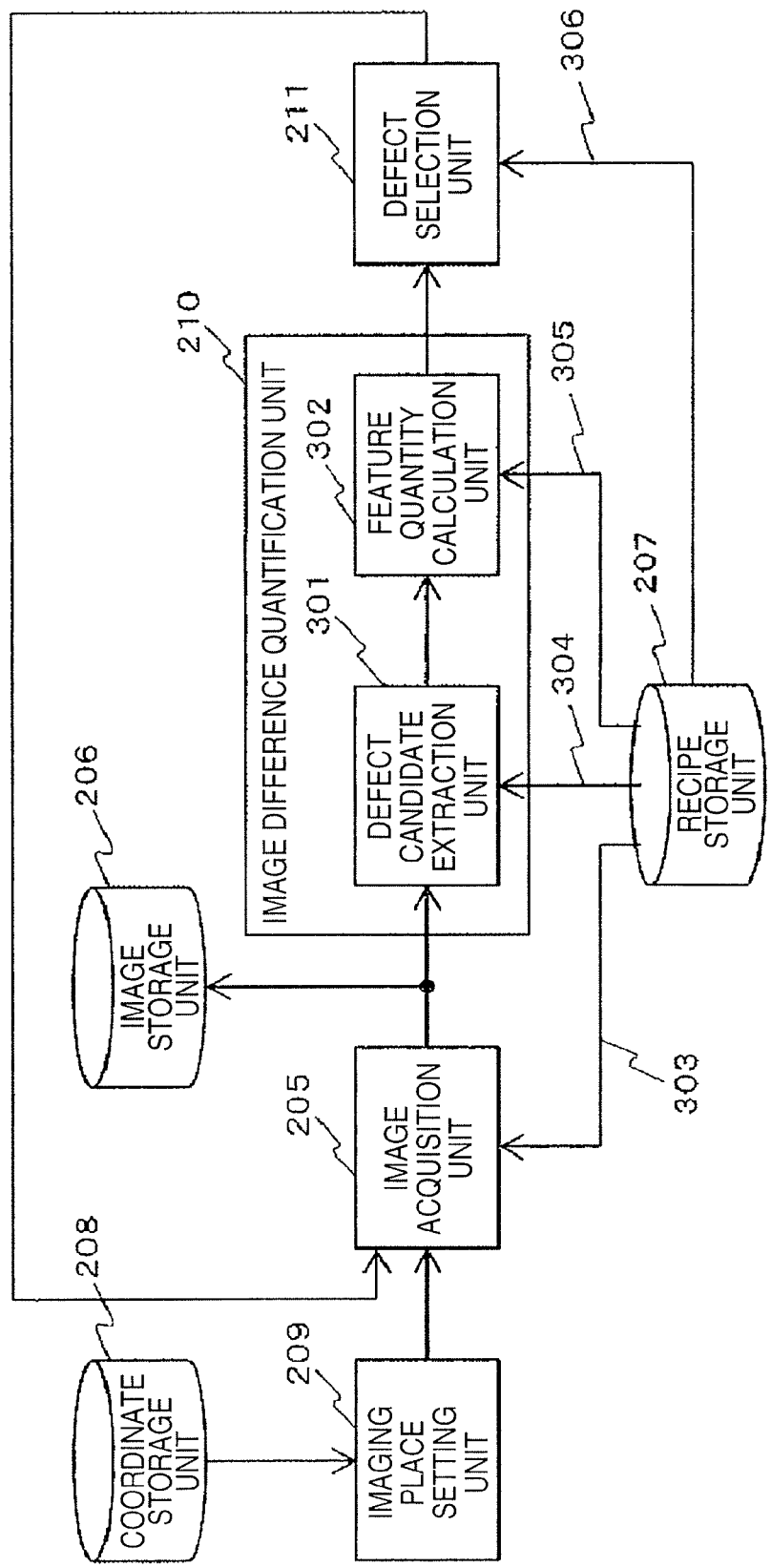
FIG. 3 is a configuration diagram for acquiring a defect observation image.

A defect observation method according to the present invention will now be described with reference to FIGS. 3 and 4. First, a defect position coordinate, which is output by a different defect inspection device, is read from the coordinate storage unit. All of the read defect position coordinates may be set to be observation object, or defect position coordinates sampled on the basis of conditions specified by the user may be set to be observation object. Subsequently, an imaging coordinate of a reference image is set by using the imaging place setting unit 209 (S401). As for the reference image, it is necessary to pick up an image of a place designed to form the same circuit pattern as that around the defect position. In the semiconductor wafer, a plurality of chips designed to form a similar circuit pattern thereon are disposed on the wafer. As the simplest method, therefore, a coordinate displaced from the defect position coordinate by a coordinate corresponding to one chip can be set as an imaging coordinate of the reference image. Then, the reference image and the defect image are picked up by using the image acquisition unit 205 (S402, S403). Then, in the image difference quantification unit 210, areas that become defect candidates are extracted by using a detect candidate extraction unit 301, and feature quantities of respective defect candidate areas are calculated by using a feature quantity calculation unit 302 (S404). Then, a defect is selected from among defect candidates by using the defect selection unit 211 (S405). It is determined whether there is the selected defect (S406). An image of the selected defect position is picked up and an image for defect observation is obtained (S407). By the way, parameters of each processing are stored in the recipe storage unit 207, and are read as occasion demands. For example, in the image acquisition unit 205, electro-optical system conditions (such as, for example, a probe current and an acceleration voltage), the number of added frames, and so forth are read out (303). Furthermore, in the defect candidate extraction unit 301, comparative processing parameters (such as, for example, a detection threshold and an image mixture rate) are read out (304). Furthermore, in the feature quantity calculation unit 302, image processing parameters (such as, for example, light and shade smoothing degree) are read out (305). Furthermore, in the defect selection unit, selection conditions (such as, for example, discrimination surfaces of defect and nuisance, an origin and shape of nuisance distribution, and a threshold for distance) are read out (306). These processing parameters concerning the image acquisition unit, the defect candidate extraction unit, the feature quantity calculation unit, and the defect selection unit are parameters concerning observation processing.

Figure 5:
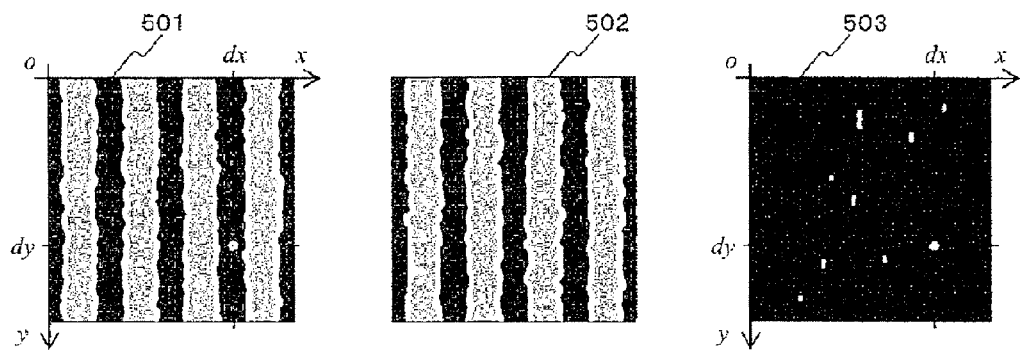
FIG. 5 is a schematic diagram representing an SEM image and a defect candidate extraction result.

The defect candidate extraction unit 301 will now be described with reference to FIG. 5. Image 501 schematically represents a defect image. Image 502 schematically represents a reference image. In the image 501, a defect exists on a coordinate (dx, dy). Image 503 represents extraction results of defect candidates. Areas where a light and shade difference between the defect image and the reference image is large are represented by a white color. Each of the extracted areas is a defect candidate. Defect candidates caused by the line edge roughness are extracted in areas other than the defect region (dx, dy). The feature quantity calculation unit 302 in the subsequent stage calculates a feature quantity with respect to each defect candidate.

Figure 6:
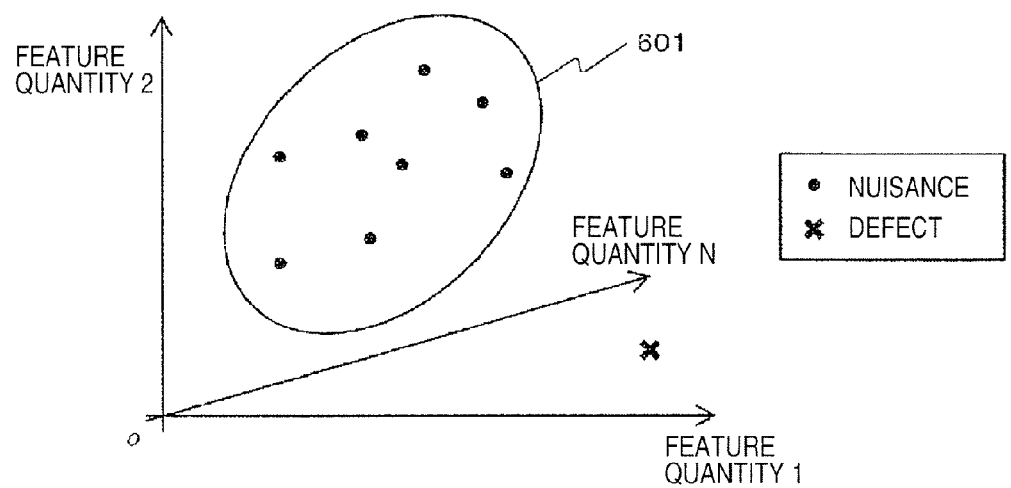
FIG. 6 is a schematic diagram representing a feature quantity space.

The defect selection unit 211 will now be described as supplement with reference to FIG. 6. FIG. 6 represents an example in which respective defect candidates are plotted in a feature quantity space. The defect selection unit 211 selects defects on the basis of feature quantities of respective defect candidates. FIG. 6 shows how defects and nuisances stored in the recipe storage unit 207 are discriminated by using a separating hyper-plane 601. By the way, defects may be selected by using a method other than the method of discriminating by using the separating hyper-plane. For example, as a simpler method, it is possible to store the center of nuisance distribution in the recipe storage unit 207 and judge a candidate having the largest distance from the center to be a defect. Or it is possible to use a configuration in which n higher order defect candidates are judged as defects and n images for defect observation are acquired. Furthermore, it is not necessary to use all feature quantities calculated by the feature quantity calculation unit 302, but feature quantity selection techniques may be combined and used.

Heretofore, the defect observation method according to the present invention has been described. In the present method, it is necessary to set processing parameters suitably for re-detecting defects with high sensitivity. For example, in a case where a detection threshold is set to be higher than a proper value (a sensitivity is set to be a lower value) in the image difference quantification unit 210, a defect candidate (area) is not extracted in a defect region. To the contrary, in a case where the detection threshold is set to be lower (the sensitivity is set to be higher), a large number of defect candidates are extracted and false discrimination is caused in the defect selection unit 211. Furthermore, in a case where the separating hyper-plane between defects and nuisances is not set suitably in the defect selection unit 211, overlooking of defects and false detection are caused. The present invention provides a method that makes it possible for the user to set parameters in the image difference quantification unit 210 and the defect selection unit 211 easily. Hereafter, a concrete method, and device configuration will be described.

Figure 7:
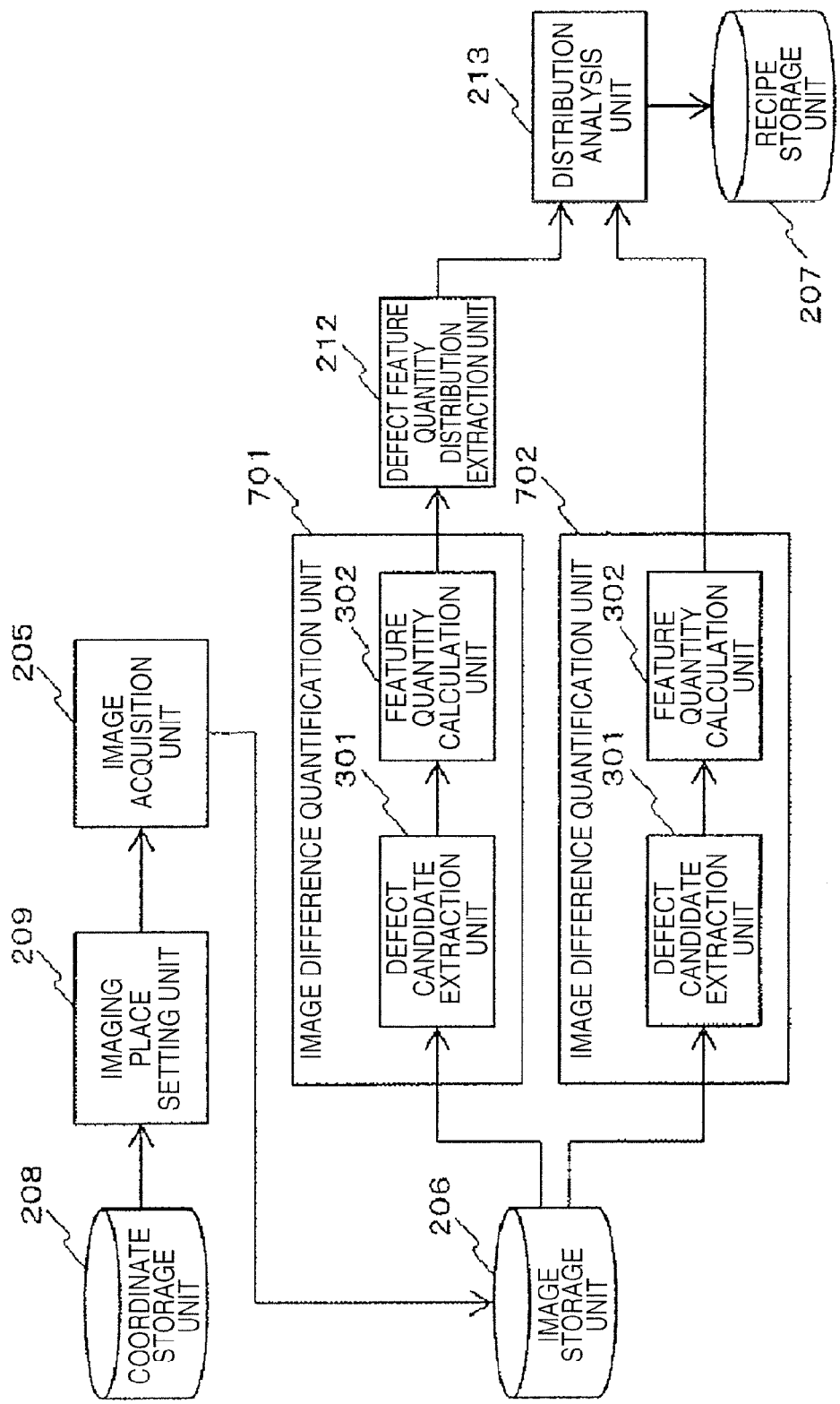
FIG. 7 is a configuration diagram for adjusting parameters.
Figure 8:
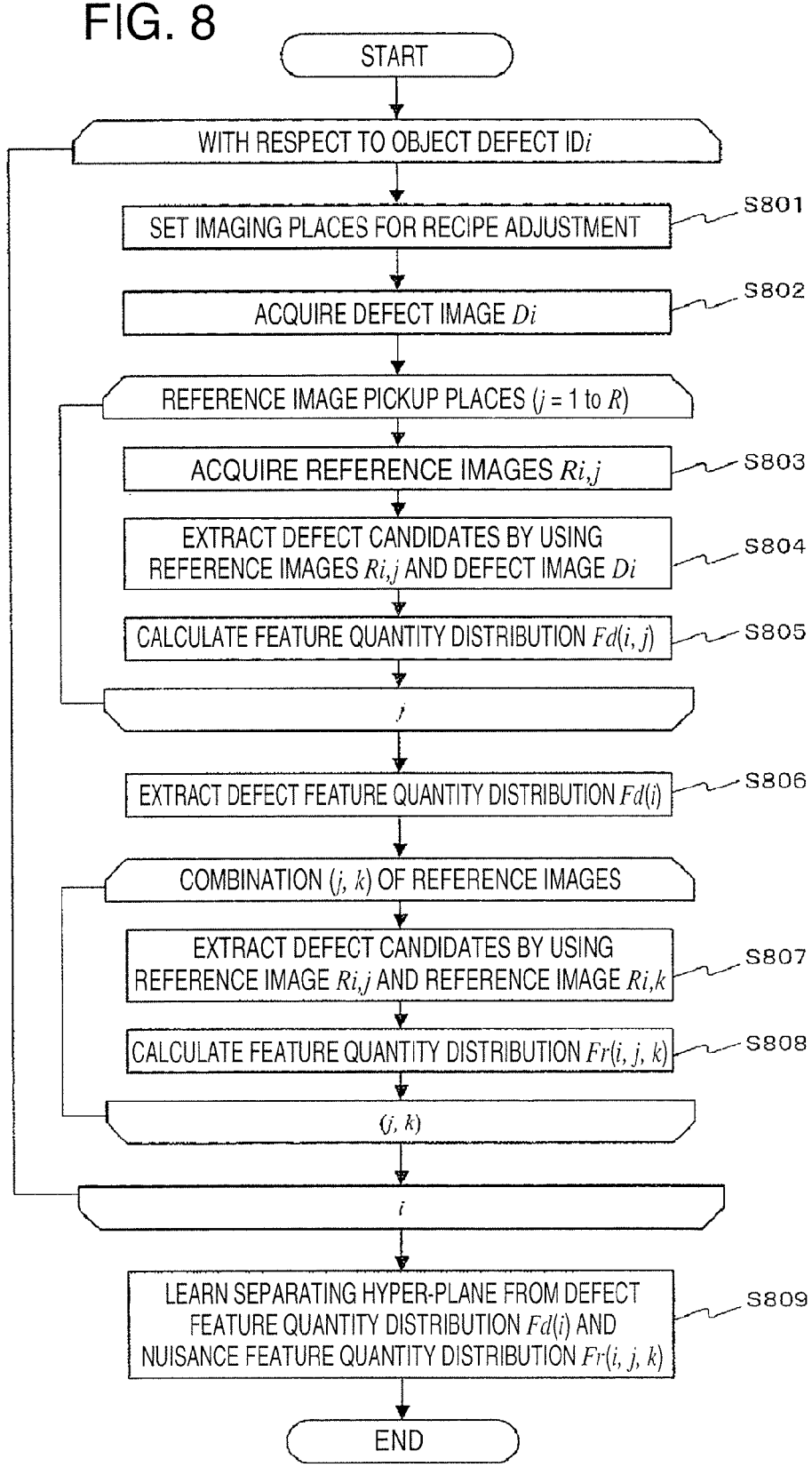
FIG. 8 is a processing flow for adjusting parameters.

A configuration, and method, for adjusting parameters in the detect selection unit 211 among processing parameters according to the present invention will now be described with reference to FIGS. 7 and 8. First, a defect position coordinate that is output by the different inspection device is read. Then, with respect to a defect that becomes an object, coordinates of R places where a reference image is to be picked up are set on the basis of the defect position coordinate by using the imaging place setting unit 209 (S801). Then, a defect image Di is picked up by using the image acquisition unit 205 (S802). Then, with respect to the set imaging places of the reference image, reference images Ri,j (j=1 to R) are acquired by using the image acquisition unit 205. Then, feature quantity distribution of a defect is calculated. Specifically, the image difference quantification unit 701 extracts defect candidates from the defect image Di and the reference images Ri,j (S804), and calculates a feature quantity Fd(i, j) of each defect candidate area (S805). Then, feature quantity distribution Fd(i) of a detect is extracted by using the defect feature quantity distribution extraction unit 212 (S806). Then, feature quantity distribution of a nuisance is calculated by using a combination (j, k) of reference images Ri (i=1 to R) picked up. Specifically, the image difference quantification unit 702 extracts defect candidates from a reference image Ri,j (j=1 to R) and a reference image Ri,k (k=j+1 to R) (S807), and calculates a feature quantity Fr(i, j, k) of each defect candidate area (S808).

The imaging place setting unit 209 calculates an area designed to form the same circuit pattern as that around a defect position. As a simple method, it is possible to select R chips located nearest the chip including the defect position coordinate and calculate a coordinate corresponding to the defect position in each chip. If the size of one chip is already known, the coordinate can be calculated easily by conducting addition and subtraction on the defect position coordinate. By the way, a search may be conducted from around the defect position by using design information of the sample.

Figure 9:
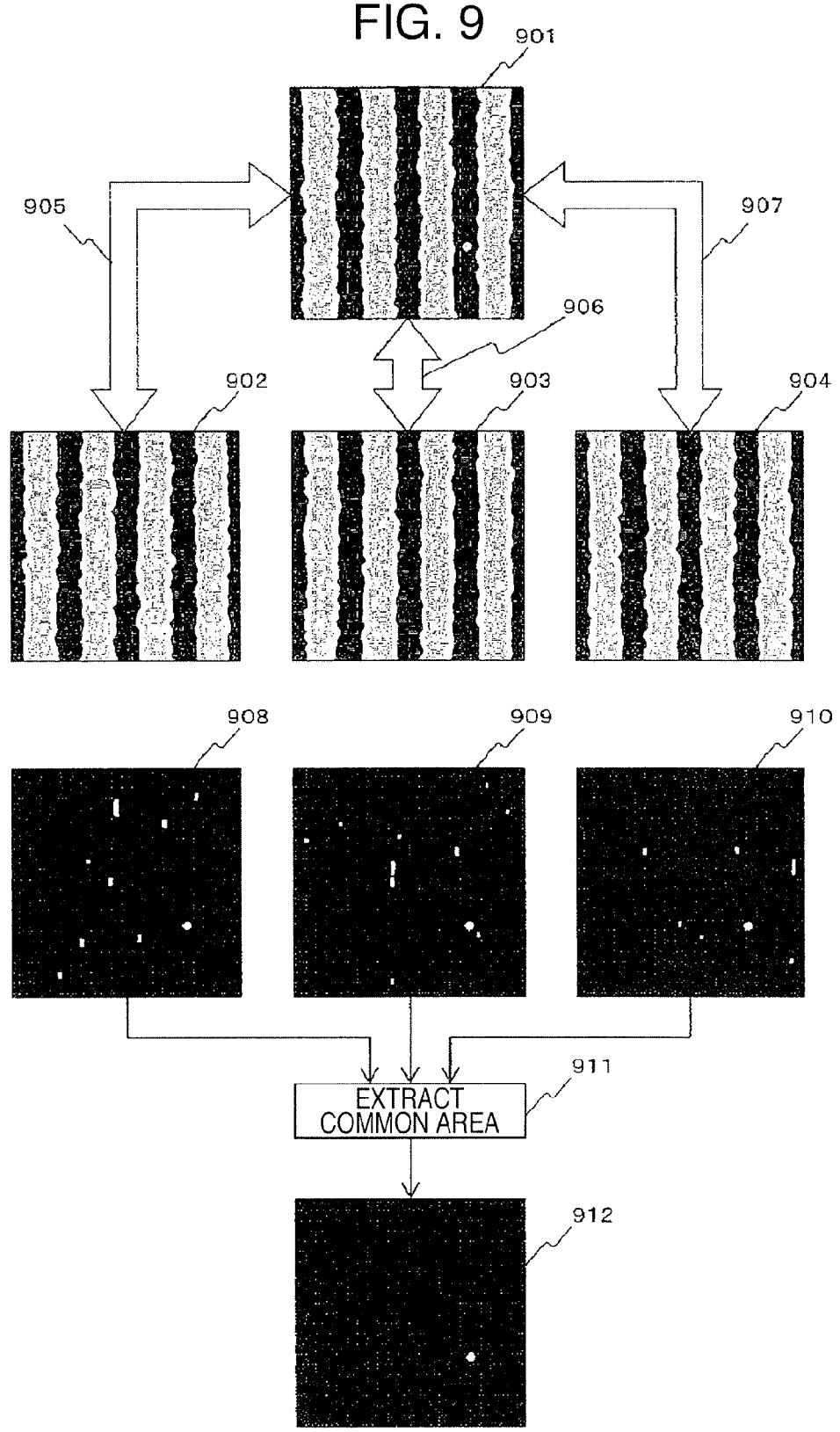
FIG. 9 shows an example in which a defect is extracted by using a plurality of reference images.

The defect feature quantity distribution extraction unit 212 will now be described with reference to FIG. 9. An image 901 schematically represents a defect image (Di). Images 902 to 904 schematically represent reference images (Ri,1 to Ri,3) in a case where R=3. An image 908 is a result of defect candidate extraction 905 using the defect image 901 and the reference image 902. Images 909 and 910 are also results of defect candidate extraction 906 and 907 in the same way. Manufacture tolerances such as line edge roughness occur at random. If only an area common to defect candidate extraction results 908 to 910 is extracted (911), therefore, defect candidates occurring at random are excluded and it becomes possible to extract only a defect (912). By the way, the detect candidate judged to be a detect may not be common to all defect detection results. In other words, if the defect candidate coincides in extraction results of at least a determinate number among a plurality of defect candidate extraction results, the defect candidate may be judged as a defect. Furthermore, the determinate number may be specified by a ratio to the number R of defect candidate extraction results. From feature quantities Fd(i, j) (j=1 to 3) calculated on the basis of this result, a feature quantity Fd(i) labeled with "defect" can be extracted. By the way, a method for extracting the feature quantity Fd(i) labeled with "defect" is not restricted to this, but, for example, distribution that is close in the feature quantity space may be extracted.

Figure 10:
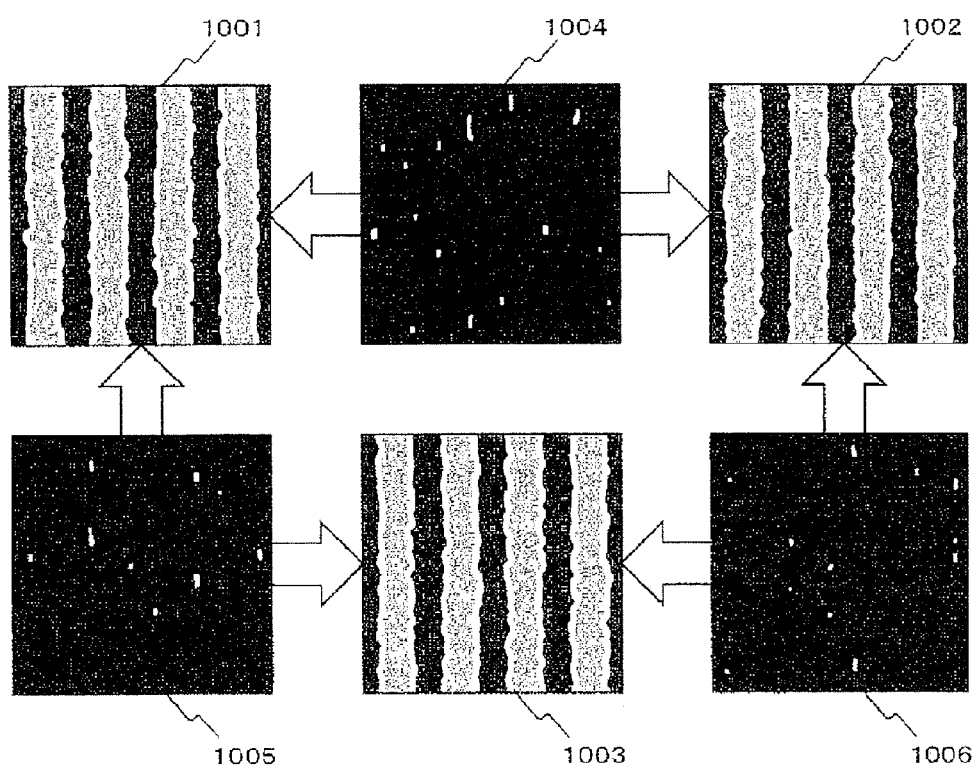
FIG. 10 shows an example in which a nuisance is extracted by using a plurality of reference images.

The method for calculating feature quantity distribution of a nuisance by using a combination (j, k) of reference images RI (i=1 to R) picked up will now be described as supplement with reference to FIG. 10. Images 1001 to 1003 schematically represent the reference images (Ri,1 to Ri,3). An image 1004 represents a defect candidate extraction result using the reference image 1001 and the reference image 1002. In the same way, an image 1005 represents a defect candidate extraction result using the reference image 1001 and the reference image 1003, and an image 1006 represents a defect candidate extraction result using the reference image 1002 and the reference image 1003. A defect is not included in a defect candidate extracted from a combination of reference images. Therefore, feature quantity distribution calculated from defect candidates included in the images 1004 to 1006 is feature quantity distribution labeled with "nuisance."

Referring back to FIG. 8, description will be continued. The above-described processing S801 to S808 is executed repeatedly with respect to defect position coordinates of M points of the observation object. As a result, defect feature quantity distribution Fd(i) and nuisance feature quantity distribution Fr(i, j, k) are obtained (where i=1 to M, and (j, k) is a combination of reference images). A separating hyper-plane for discriminating defects and nuisances is learned on the basis of the obtained distribution by using the distribution analysis unit 213 (S809). As a method of learning, the technique of pattern recognition can be used. Specifically, the neural network may be used or the SVM may be used. Or an algorithm (such as, for example, C4.5) for automatically generating a discrimination rule may be used. Or the separating hyper-plane is not calculated, but it is possible to store labeled feature quantity distribution and discriminate by using the k-nearest neighbor algorithm or the like at the time of discrimination. By the way, the calculated separating hyper-plane or parameters required for discrimination are stored in the recipe storage unit 207.

Figure 11:
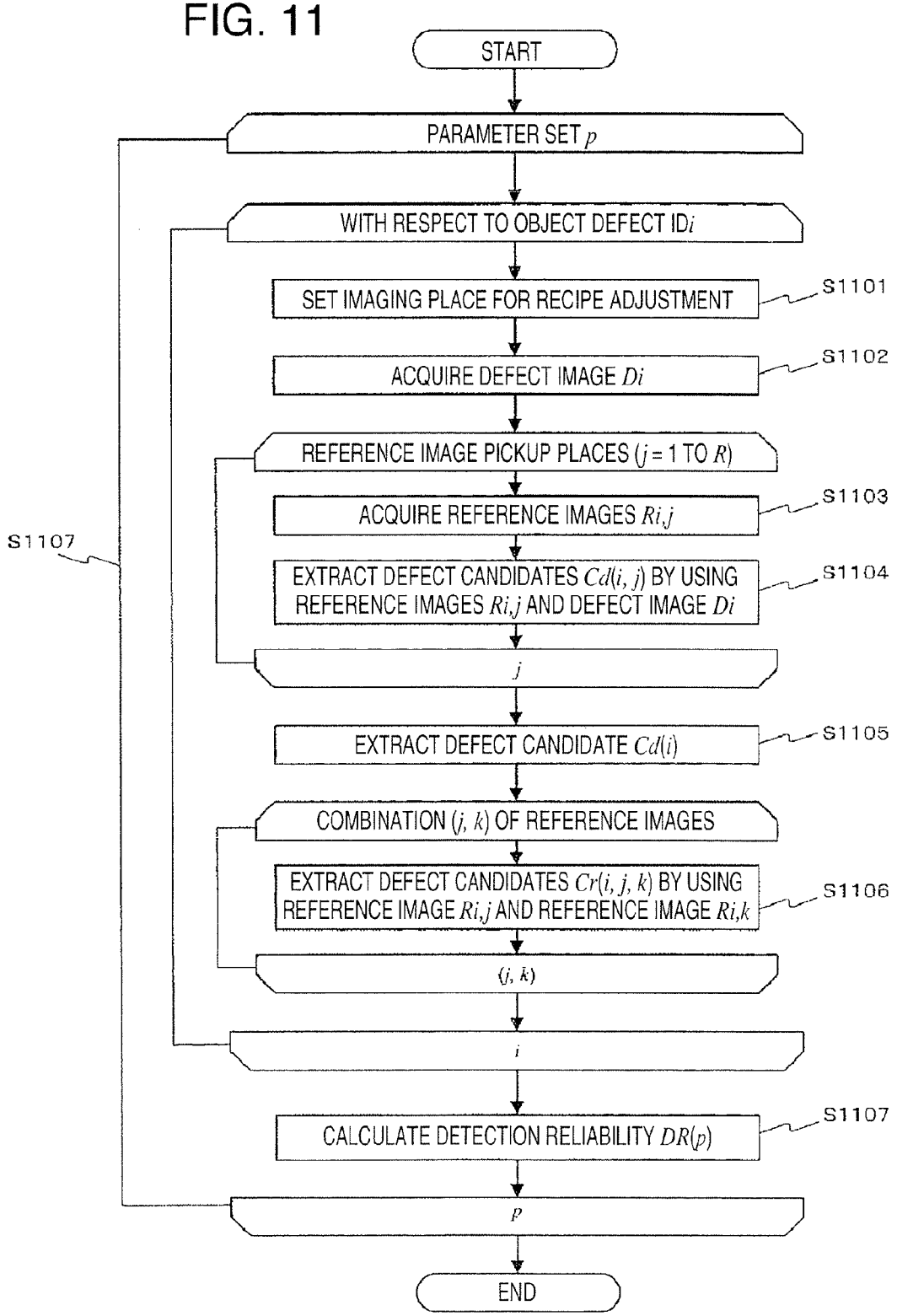
FIG. 11 is a processing flow for adjusting parameters.

Heretofore, the method for adjusting the parameters in the defect selection unit 211 has been described. A method for adjusting parameters in the image difference quantification unit 210 will now be described. Previously, an outline will be described. Defect detection is conducted by using a combination of parameters (such as, for example, a detection threshold and an image mixture rate) concerning the image difference quantification unit 210. A parameter having a high defect detection rate is searched. At this time, it becomes possible to calculate a defect detection rate having a high probability by using a plurality of reference images. Hereafter, details of the processing will be described with reference to FIG. 11. By the way, the parameter adjustment in the defect selection unit 211 and the parameter adjustment in the image difference quantification unit 210 may be conducted in parallel simultaneously, or may be conducted one after another. By the way, in a case the parameter adjustments are conducted one after another, either of them may be conducted earlier in execution order. Or only one of them may be conducted.

First, with respect to an object defect, image pickup places of reference images are set by using the imaging place setting unit 209 (S1101). A defect image Di is acquired by using the defect acquisition unit 205 (S1102). By the way, in a case where it can be judged in the defect acquisition unit 205 that a defect image of a pertinent defect ID is already picked up, an image may be read from the image storage unit. Then, R reference images Ri,j (j=1 to R) are acquired by using the image acquisition unit 205 (S1103). Then, defect candidates Cd(i, j) are extracted by using the defect image Di and the reference images Ri,j (S1104). Then, a defect candidate Cd(i) is extracted from a plurality of obtained defect candidates Cd(i, j) (j=1 to R) (S1105). As one method for extraction, only a common defect candidate area can be extracted as shown in FIG. 9. A defect candidate included in Cd(i) can be supposed to be a defect by using a result of a plurality of reference images as described above. Then, defect candidates Cr(i, j, k) are extracted by using a combination (j, k) of reference images Ri (i=1 to R) (S1106). Because of extraction results using only reference images, a defect candidate included in the defect candidates Cr(i, j, k) can be supposed to be a nuisance. Then, detection reliability DRp is calculated (S1107). DR(p) is an index representing reliability of a defect detection result at the time when a parameter set p is used. DR(p) can be calculated according to, for example, (MATH. 1). S1101 to S1107 described heretofore are conducted for combinations of parameters of search objects, and parameters that maximize DR(p) are found. As a result, parameters reducing defect candidates that become nuisances and raising the defect detection rate are obtained. Furthermore, parameters and DR(p) may be associated with each other and output to make it possible for the user to conduct selection.

$$DR(p) = \text{Sum total of the numbers of defect candidates included in } Cd(i)/(\text{sum total of the numbers of defect candidates included in } Cr(i,j,k)) \quad \text{(MATH. 1)}$$

Heretofore, the method for adjusting parameters in the image difference quantification unit 210 and the defect selection unit 211 has been described. By, the way, it can be implemented easily to acquire an observation image of a defect at the same time that parameters are adjusted, by utilizing the fact that a defect can be detected with high reliability by using a plurality of reference images. However, it becomes a cause of throughput lowering to pick up a plurality of reference images. After the parameter adjustment has been completed, therefore, it is desirable to conduct ordinary observation processing (using one reference image) (FIG. 4).

Figure 4:
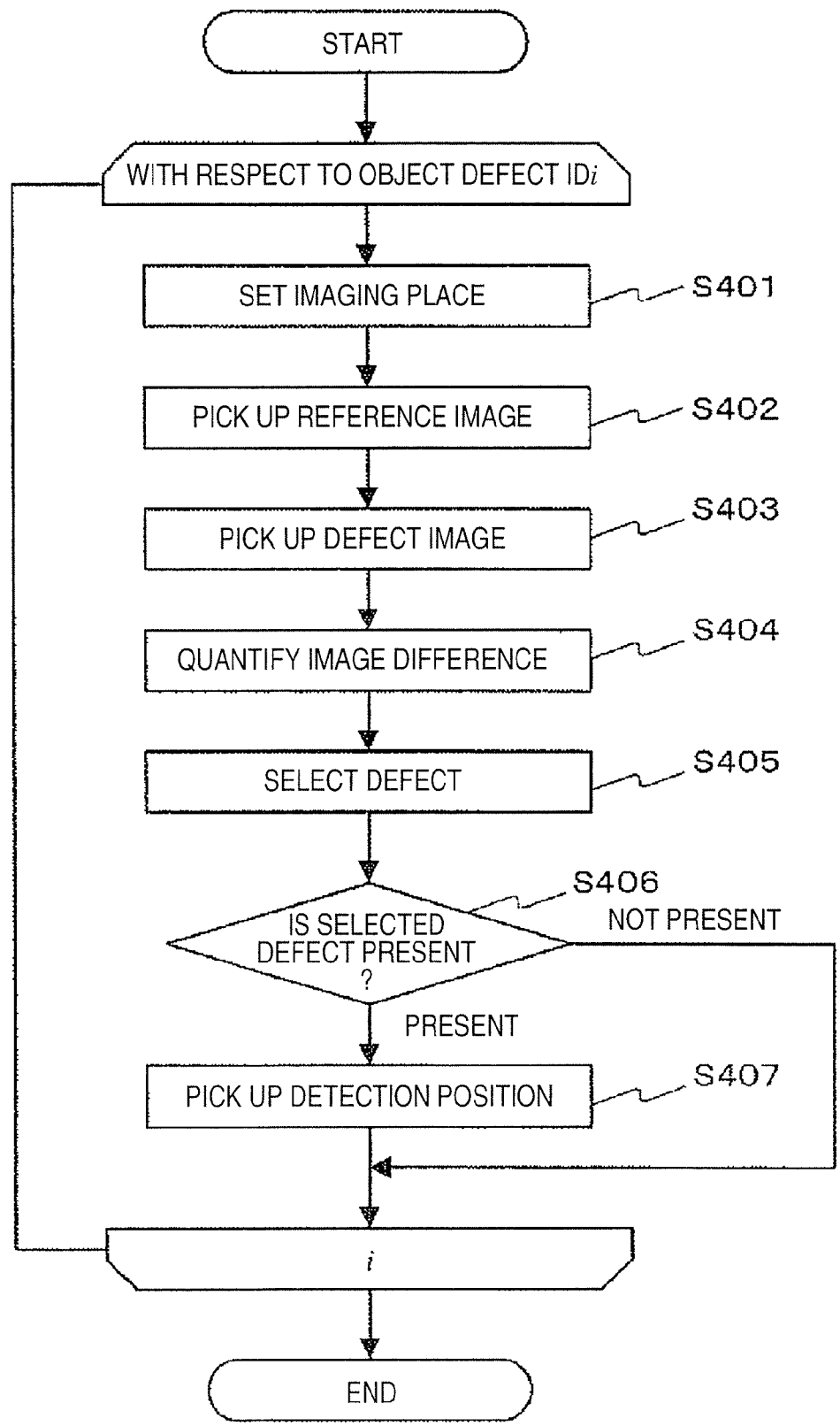
FIG. 4 is a processing flow for acquiring a defect observation image.
Figure 12:
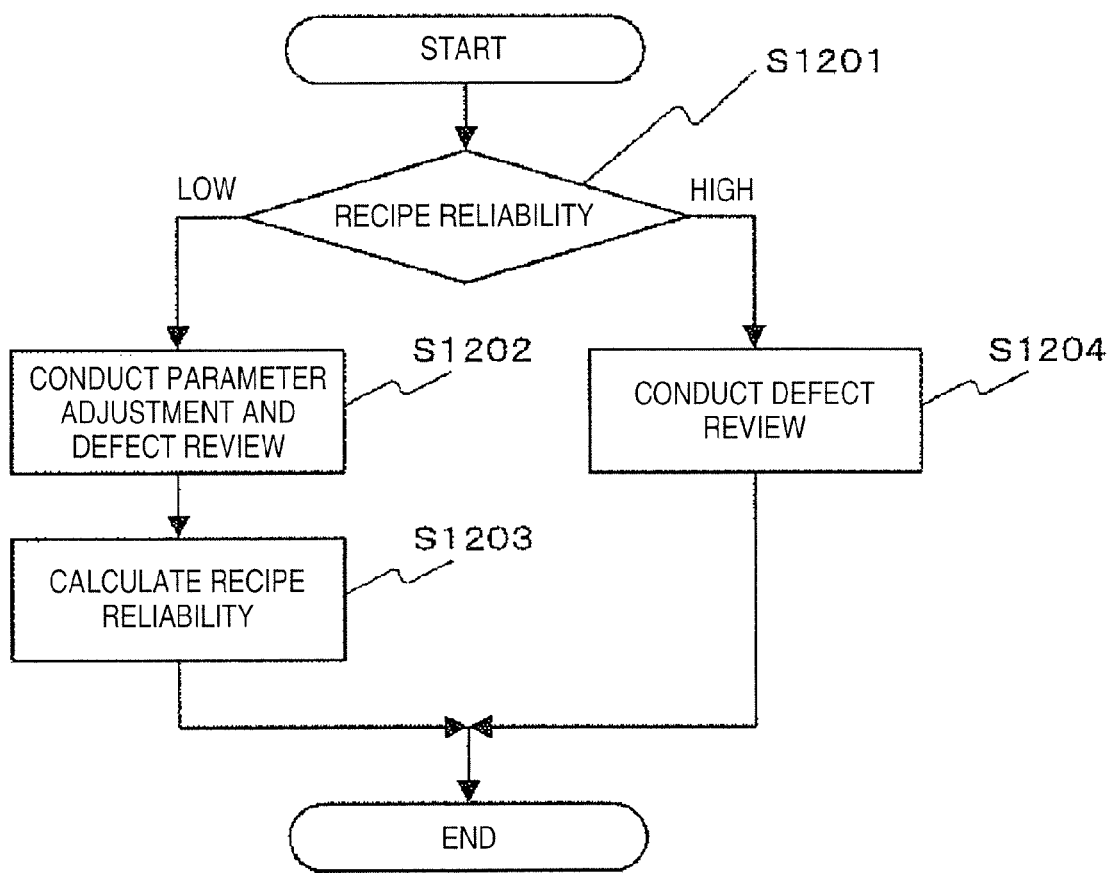
FIG. 12 is a processing flow for controlling execution of parameter adjustment.

FIG. 12 shows a method for automatically changing over between the parameter adjustment processing (FIGS. 8 and 11) and ordinary observation processing (FIG. 4). First, reliability of a recipe stored in the recipe storage unit 207 is judged (S1201). By the way, in a case where a recipe corresponding to the sample of the observation object does not exist, the reliability is also judged as low. In a case where the reliability is low, the recipe is adjusted by using the above-described recipe adjustment processing. Then, reliability of the created recipe is judged (S1202). Reliability of parameters concerning the defect selection unit 211 can be judged by conducting n-fold cross validation and evaluating stability of the defect detection rate. Furthermore, reliability of parameters concerning the image difference quantification unit 212 is can be judged by evaluating whether the defect detection rate has reached a predetermined threshold on the basis of a result of the defect candidate extraction processing (S1105) using a plurality of reference images and a defect image. In a case where reliability is judged as high in the recipe reliability decision processing, ordinary observation processing (S1204) is conducted using adjusted parameters when observing samples of observation object thereafter. By the way, it is also possible to record date and hour of recipe creation and judge the reliability as low in the recipe reliability decision processing (S1201) in a case where a determinate period has elapsed from the time of recipe creation.

The parameter adjustment method in the case where defect candidates are extracted on the basis of the defect image and the reference images picked up has been described. However, the method can also be utilized in parameter adjustment in a case where defect detection is conducted from one defect image by using, for example, the method stated in Patent Literature 3. In this case, in the processing (S807, S1106) for extracting defect candidates that become nuisances, defect candidates should be extracted by using reference images synthesized from reference images picked up and the reference images picked up. Furthermore, in the processing (S804, S1104) for extracting defect candidates from a defect image, defect candidates may be extracted by using reference images synthesized from reference images picked up and the reference images picked up. By doing so, it becomes also possible to cope with a case where the feature quantity distribution of nuisances changes according to the synthesis precision of the reference image. Furthermore, it also becomes possible to adjust parameters concerning synthesis processing of the reference images.

Furthermore, an image generated on the basis of design information of the sample may be used as a reference image. At this time, a plurality of reference images generated by changing parameters at the time when generating an image from design information may be used. By doing so, it becomes possible to adjust parameters at the time when detecting defect candidates by using a defect image picked up and an image generated on the basis of design information of the sample.

Figure 13:
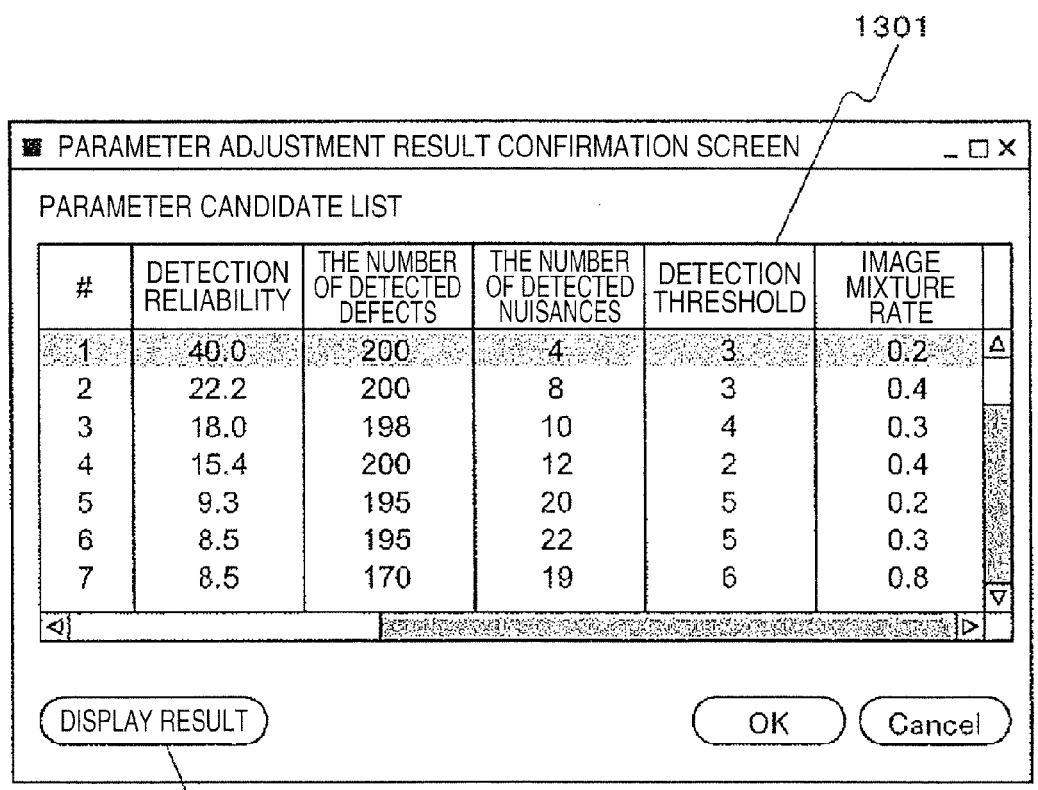
FIG. 13 is a GUI for displaying a result of parameter adjustment.

A user interface of the defect observation device according to the present invention will now be described. FIG. 13 shows an example of a GUI, which displays a list of parameters searched for, in association with detection reliability, the number of detected defects, and the number of detected nuisances. In a parameter list display portion 1301, the user can select a parameter. Furthermore, a button 1302 is provided to call a GUI for confirming a defect detection result in a case where a selected parameter is used. FIG. 14(a) shows an example of a GUI for confirming a defect detection result. A selection portion 1401 is provided to select a defect ID, and a display portion 1402 is provided to display an image and calculated feature quantities. In the display portion 1402, display contents can be changed over by using an "image tab" 1403 and a "feature quantity tab" 1404. In a case where the image tab is effective, a selection portion 1405 is provided to select a displayed image, a selection portion 1406 is provided to specify a displayed image detector (a secondary electron image or a reflected electron image), a selection portion 1407 is provided to specify whether to overlay display a defect candidate detection result on an image, and a display portion 1408 is provided to display an image. Furthermore, it may be made possible to display two images or feature quantities side by side and confirm them by providing a second display portion 1409 to display an image and a calculated feature quantity. FIG. 14(b) shows an example of a GUI in a case where the "feature quantity tab" is made effective in the second display portion 1408. A specification portion 1410 is provided to specify an abscissa axis and an ordinate axis of a displayed feature quantity space, and a display portion 1411 is provided to display a result obtained by plotting defect candidates in the feature quantity space. Furthermore, a separating hyper-plane 1412 in the feature quantity space may be displayed. By the way, not the feature quantity space, but a histogram of a specified feature quantity may be displayed.

As described heretofore, it becomes possible to extract defect candidates that can be labeled easily with "defect" and "nuisance" from the sample of observation object by using a defect image and a plurality of reference images. As a result, it becomes possible to adjust easily the parameter used to extract defect candidates and the separating hyper-plane used to separate defect candidates into defects and nuisances. Furthermore, it becomes possible to re-detect defects with high sensitivity by storing adjusted parameters into a recipe.

Embodiment 2

In embodiment 1, the method of extracting defect candidates that can be labeled easily with "defect" and "nuisance" from the sample of observation object on the basis of a defect image and a plurality of reference images and adjusting parameters concerning defect re-detection has been described. In embodiment 2, a method of extracting defect candidates that can be labeled easily with "nuisance" from the sample of observation object on the basis of a plurality of reference images and adjusting parameters concerning defect re-detection will be described.

A device configuration according to the present embodiment is similar to that shown in FIGS. 1 and 2. Furthermore, as regards a user interface as well, a user interface similar to that shown in FIGS. 13 and 114 is provided. The present embodiment differs from embodiment 1 in a flow concerning parameter adjustment in the defect selection unit 211. Hereafter, only a portion where the present embodiment differs from embodiment 1 will be described.

First, as for places designed to form similar circuit patterns, R points are extracted and imaging places are set (S1501). At this time, imaging places are set to prevent a defect from being included in images picked up, on the basis of defect position coordinates that are output by a different defect inspection device. Then, images Ri,j (j=1 to R) in set imaging places are acquired by using the image acquisition unit 205 (S1502). Then, with respect to a combination (j, k) of images picked up, defect candidates are extracted and feature quantity distribution Fr(i, j, k) of the extracted defect candidates is calculated by using the image difference quantification unit 210. S1501 to S1504 described heretofore are conducted repeatedly with respect to N points (S1505). Since a defect is not included in acquired images, the feature quantity distribution Fr(i, j, k) becomes feature quantity distribution labeled with "nuisance."

Therefore, it becomes possible to obtain a separating hyper-plane for discriminating defects and nuisances, by using the nuisance feature quantity distribution Fr(i, j, k) and the technique of pattern recognition and configuring a one-class classifier (S1506). Furthermore, parameters (such as, for example, the origin position and variance) of nuisance distribution may be found without finding a separating hyper-plane.

As described heretofore, it becomes possible to extract defect candidates that can be labeled easily with "nuisance" from the sample of observation object by using a plurality of reference images. As a result, it becomes possible to adjust easily the separating hyper-plane that distinguishes nuisances from defect candidates. Furthermore, it becomes possible to re-detect defects with high sensitivity by storing adjusted parameters into the recipe.

REFERENCE SIGNS LIST

101: Scanning electron microscope (SEM)
112: Image generation unit
206: Image storage unit
207: Recipe storage unit
208: Coordinate storage unit
209: Imaging place setting unit
210: Image difference quantification unit
211: Defect selection unit
212: Defect feature quantity distribution extraction unit
213: Distribution analysis unit
301: Defect candidate extraction unit
302: Feature quantity calculation unit
S404: Step of conducting defect candidate extraction and feature quantity calculation
S405: Step of selecting a defect
S802: Step of picking up a defect image
S803: Step of picking up a plurality of reference images
S805: Step of finding a comparative inspection result between a reference image and a defect image
S808: Step of finding a comparative inspection result between a reference image and a reference image
S809: Step of calculating a separating hyper-plane
S1202: Step of adjusting parameters

The invention claimed is:

1. A defect observation method, comprising:
    imaging an inspection object using an optical device or a charged particle beam device on the basis of defect information received from an inspection device and obtaining a defect image and a reference image corresponding to the defect image,
        the reference image including a plurality of reference images, and
        the plurality of reference images being different images of an area on the inspection object designed to form a same circuit pattern without defects as a pattern intended in an area of the defect image;
    performing a parameter adjustment process for determining a first parameter to be used in defect extraction by using first feature quantity distribution obtained from the defect image by said imaging and the reference image and a second feature quantity distribution obtained from the plurality of reference images,
        the second feature quantity distribution being a feature quantity distribution in an area judged as a defect candidate in any of the difference images between the plurality of reference images; and
    performing an observation process for conducting observation of the inspection object using the optical device or charged particle beam device using the first parameter to generate a plurality of defect candidates occurring in the inspection object,
    wherein said parameter adjustment process further comprises determining a separating hyperplane based on said first feature quantity distribution and said second feature quantity distribution, and
    wherein said observation process further comprises discriminating between nuisances and defects among said plurality of defect candidates based on the first parameter and the separating hyperplane.

2. The defect observation method according to claim 1, wherein in the parameter adjustment process, the first feature quantity distribution is determined by using difference images between the defect image and the respective reference images.

3. The defect observation method according to claim 2, wherein the first feature quantity distribution is feature quantity distribution in an area judged as a defect candidate in common in difference images between the defect image and the respective reference images.

4. The defect observation method according to claim 1, wherein the parameter adjustment process further comprises using a second parameter for defect extraction determined on the basis of the first feature quantity distribution, the second feature quantity distribution, and a defect detection rate.

5. The defect observation method according to claim 1, wherein in the observation process, at least one of the defect image and the reference image picked up in the imaging is used.

6. The defect observation method according to claim 1, wherein the defect information is information concerning a position of a defect.

7. A defect observation device, comprising:
a scanning electron microscope configured to produce an image of an inspection object on the basis of defect information received from an inspection device and to obtain a defect image and a reference image corresponding to the defect image,
the reference image including a plurality of reference images, and the plurality of reference images being different images of an area on the inspection object designed to form a same circuit pattern without defects as a pattern intended in an area of the defect image; and
a defect feature extractor configured to determine and to adjust a first parameter to be used in defect extraction using a first feature quantity distribution obtained from the defect image picked up by the scanning electron microscope and the reference image and a second feature quantity distribution obtained from the plurality reference images,
the second feature quantity distribution being a feature quantity distribution in an area judged as a defect candidate in any of the difference images between the plurality of reference images,
wherein the scanning electron microscope is further configured to conduct observation of the inspection object using the first parameter to generate a plurality of defect candidates occurring in the defect object,
wherein said defect feature extractor is further configured to adjust said first parameter using a separating hyperplane which is determined based on said first feature quantity distribution and said second feature quantity distribution, and
wherein said scanning electron microscope is further configured, during said observation of the inspection object, to discriminate between nuisances and defects among said plurality of defect candidates based on the first parameter and the separating hyperplane.

8. The defect observation device according to claim 7, wherein the defect feature extractor is further configured to determine the first feature quantity distribution is difference images between the defect image and the respective reference images.

9. The defect observation device according to claim 8, wherein the first feature quantity distribution is feature quantity distribution in an area judged as a defect candidate in all difference images between the defect image and the respective reference images.

10. The defect observation device according to claim 7, wherein the defect feature extractor is further configured to determine a second parameter used in defect extraction on the basis of the first feature quantity distribution, the second feature quantity distribution, and a defect detection rate.

11. The defect observation device according to claim 7, wherein the scanning electron microscope is further configured to use at least one of the defect image and the reference image.

12. The defect observation device according to claim 7, wherein the defect information is information concerning a position of a defect.

* * * * *